(12) United States Patent
Schofield et al.

(10) Patent No.: US 8,492,352 B2
(45) Date of Patent: Jul. 23, 2013

(54) POLYSACCHARIDES WITH ANTITHROMBOTIC ACTIVITY, INCLUDING A COVALENT BOND AND AN AMINO CHAIN

(75) Inventors: Joseph Schofield, Paris (FR); Dave Smith, Paris (FR); Patrick Soubayrol, Paris (FR)

(73) Assignee: Sanofi, Paris (FR)

( * ) Notice: Subject to any disclaimer, the term of this patent is extended or adjusted under 35 U.S.C. 154(b) by 8 days.

(21) Appl. No.: 13/060,810

(22) PCT Filed: Aug. 24, 2009

(86) PCT No.: PCT/FR2009/001023
§ 371 (c)(1),
(2), (4) Date: Aug. 31, 2011

(87) PCT Pub. No.: WO2010/023374
PCT Pub. Date: Mar. 4, 2010

(65) Prior Publication Data
US 2011/0306567 A1    Dec. 15, 2011

(30) Foreign Application Priority Data
Aug. 26, 2008   (FR) ..................................... 08 04704

(51) Int. Cl.
*A61K 31/7028* (2006.01)
*A61K 31/715* (2006.01)
*A61K 31/70* (2006.01)
*A61K 31/702* (2006.01)
*C07H 3/06* (2006.01)
*C07H 15/04* (2006.01)
*A61P 7/02* (2006.01)

(52) U.S. Cl.
USPC ................ 514/25; 514/54; 514/42; 536/55.1; 536/54; 536/17.5; 536/4.1; 536/18.7; 536/122; 536/17.2; 536/22.1

(58) Field of Classification Search
USPC ................... 514/54, 25, 56, 42; 536/55.1, 54, 536/17.5, 4.1, 18.7, 122, 17.2, 21, 22.1
See application file for complete search history.

(56) References Cited

FOREIGN PATENT DOCUMENTS
WO    WO 02/24754    3/2002

OTHER PUBLICATIONS

Trisha Gura; Science. vol. 278, Nov. 7, 1997.*
International Search Report dated Dec. 3, 2009.

* cited by examiner

*Primary Examiner* — Shaojia Anna Jiang
*Assistant Examiner* — Michael C Henry
(74) *Attorney, Agent, or Firm* — Scully, Scott, Murphy & Presser, P.C.

(57) ABSTRACT

The present invention relates to novel synthetic polysaccharides with antithrombotic activity, having at least one covalent bond with an amino chain, and to the preparation method thereof and to the therapeutic use thereof.

10 Claims, No Drawings

POLYSACCHARIDES WITH ANTITHROMBOTIC ACTIVITY, INCLUDING A COVALENT BOND AND AN AMINO CHAIN

The present invention relates to novel synthetic oligo- and polysaccharides having at least one covalent bond with an amino chain and having the anticoagulant and antithrombotic pharmacological activities of heparin.

Patent application WO 02/24754 describes synthetic polysaccharides which have a covalent bond with biotin (hexahydro-2-oxo-1H-thieno[3,4-d]imidazole-4-pentanoic acid) or with a biotin derivative. Such polysaccharides have an antithrombotic activity which makes them usable as anticoagulant agents and have, in addition, the advantage of being able to be rapidly neutralized with a specific antidote, in an emergency situation. This specific antidote is avidin (The Merck Index, Twelfth edition, 1996, M.N. 920, pages 151-152) or streptavidin, which are two tetrameric proteins of respective masses equal to approximately 66 000 and 60 000 Da, and which have a very strong affinity for biotin.

Novel polysaccharides which have structures analogous to those described in patent application WO 02/24754, but which, in place of the covalent bond with biotin, have an amino chain, have now been identified. These novel saccharides advantageously have antithrombotic properties comparable to those described in the abovementioned patent application.

Generally, the invention therefore relates to synthetic polysaccharides with antithrombotic activity, having at least one covalent bond with an amino chain of formula —NH—CO—(CH$_2$)$_5$—NH$_2$.

In particular, the subject of the present invention is the polysaccharides of formula (I):

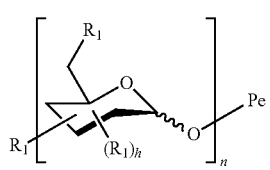
(I)

in which:
the wavy line denotes a bond located either below or above the plane of the pyranose ring, the formula:

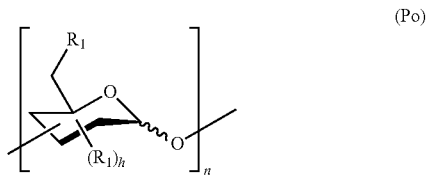
(Po)

denotes a polysaccharide containing n identical or different monosaccharide units, said polysaccharide being bonded via its anomeric carbon to Pe, the formula:

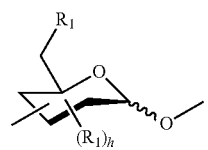

is a diagrammatic representation of a monosaccharide unit with a pyranose structure, chosen from hexoses, pentoses and the corresponding deoxy sugars, this unit being bonded via its anomeric carbon to another monosaccharide unit, and the hydroxyl groups of this unit being substituted with groups R$_1$, which may be identical or different, R$_1$ being as defined below, Pe represents a pentasaccharide having the structure:

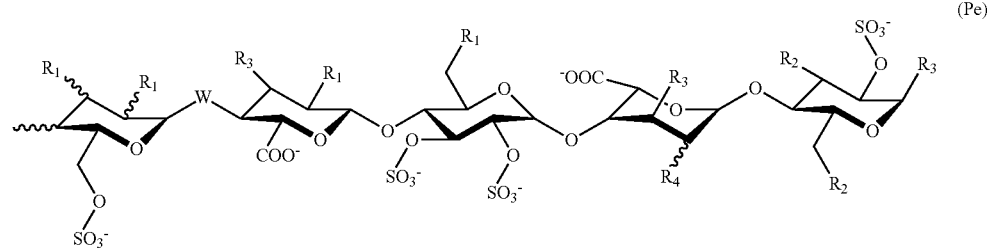
(Pe)

h is equal to 1 or 2,
n is an integer and can take any value from 0 to 25,
R$_1$ represents an —NH—CO—(CH$_2$)$_5$—NH$_2$ group, a (C$_1$-C$_6$)alkoxy group or an —OSO$_3^-$ group;
R$_2$ represents an —NH—CO—(CH$_2$)$_5$—NH$_2$ group, a (C$_1$-C$_6$)alkoxy group or an —OSO$_3^-$ group;
R$_3$ represents an —NH—CO—(CH$_2$)$_5$—NH$_2$ group or a (C$_1$-C$_6$)alkoxy group;
R$_4$ represents an —NH—CO(CH$_2$)$_5$—NH$_2$ group, a (C$_1$-C$_6$)alkoxy group or an —OSO$_3^-$ group or else R$_4$ constitutes an —OH—CH$_2$-bridge, the —CH$_2$— group being bonded to the carbon atom bearing the carboxylic function on the same ring;
it being understood that at least one of the substituents R$_1$, R$_2$, R$_3$ or R$_4$ represents an —NH—CO—(CH$_2$)$_5$—NH$_2$ group;
W represents an oxygen atom or a methylene group, and also the pharmaceutically acceptable salts thereof.

As indicated previously, it will be noted that, generally in the present description, a wavy line denotes a bond located either below or above the plane of the pyranose ring.

The monosaccharides contained in Po may be identical to or different than one another, the interglycosidic linkages may be of the α or β type.

These monosaccharides are advantageously chosen from the D or L hexoses, alone, altrose, glucose, mannose, galose, idose, galactose and talose (in this case h=2) or from the D or L pentoses, ribose, arabinose, xylose and lyxose (in this case h=2). Other monosaccharides, such as, for example, deoxy sugars, can also be used (h=1 and/or —$CH_2R_1$=$CH_3$).

The polysaccharide part Po may be constituted of 0 to 25 alkylated and di- or trisulfated monosaccharide units.

The polysaccharide part Po may also be constituted of 0 to 25 alkylated and mono- or disulfated monosaccharide units.

The polysaccharide part Po may be constituted of 0 to 25 uncharged and/or partially charged and/or totally charged alkylated monosaccharide units.

The charged or uncharged units may be dispersed all along the chain or they may, on the contrary, be grouped into charged or uncharged saccharide domains.

The linkages between the units may be 1.2; 1.3; 1.4; 1.5; 1.6; and of the α or β type.

In the present description, it has been chosen to represent the $^1C_4$ conformation for L-iduronic acid and the $^4C_1$ conformation for D-glucuronic acid, but it is common knowledge that, in general, the conformation in solution of monosaccharide units fluctuates. Thus, L-iduronic acid may be of $^1C_4$, $^2S_0$ or $^4C_1$ conformation.

According to one of its aspects, the invention relates to the polysaccharides of formula (I.1):

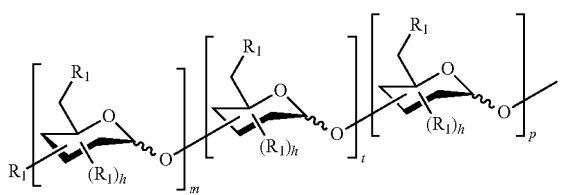

the formula:

denotes a particular family of polysaccharides Po, bonded via their anomeric carbon to Pe as defined for (I), the formula:

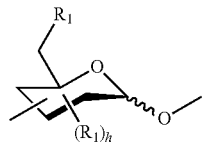

is as defined for (I), the $R_1$ groups are as defined for (I) and, for the same monosaccharide, may be identical or different, the monosaccharide contained in [ ]$_m$ is repeated m times,
the monosaccharide contained in [ ]$_t$ is repeated t times,
the monosaccharide contained in [ ]$_p$ is repeated p times, m is an integer ranging from 1 to 5, t is an integer ranging from 0 to 24 and p is an integer ranging from 0 to 24, it being understood that $1 \leq m+t+p \leq 25$, and also the pharmaceutically acceptable salts thereof.

Among these polysaccharides of formula (I.1), the polysaccharides in which just one of the substituents $R_1$, $R_2$, $R_3$ or $R_4$ represents an —NH—CO—$(CH_2)_5$—$NH_2$ group, and also the pharmaceutically acceptable salts thereof, constitute a subgroup of the invention.

in which:

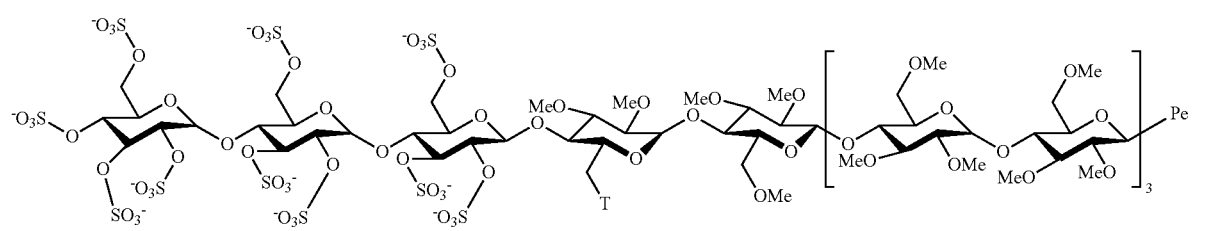

According to one particular aspect, the invention relates to the hexadecasaccharides of formula (I.2):
in which:
T represents an —NH—CO—(CH$_2$)$_5$—NH$_2$ group,
Pe represents a pentasaccharide having the structure:

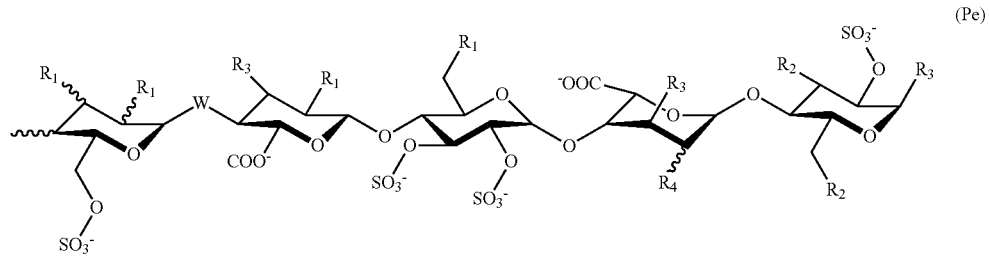
(Pe)

in which:
R$_1$ represents a (C$_1$-C$_6$)alkoxy group or an —OSO$_3^-$ group,
R$_2$ represents a (C$_1$-C$_6$)alkoxy group or an —OSO$_3^-$ group,
R$_3$ represents a (C$_1$-C$_6$)alkoxy group,
R$_4$ represents a (C$_1$-C$_6$) alkoxy group or an —OSO$_3^-$ group, or else R$_4$ constitutes an —O—CH$_2$-bridge, the —CH$_2$— group being bonded to the carbon atom bearing the carboxylic function on the same ring,
W represents an oxygen atom or a methylene group, and also the pharmaceutically acceptable salts thereof.

According to another of its aspects, the invention relates to the pentasaccharides of formula (I.3):

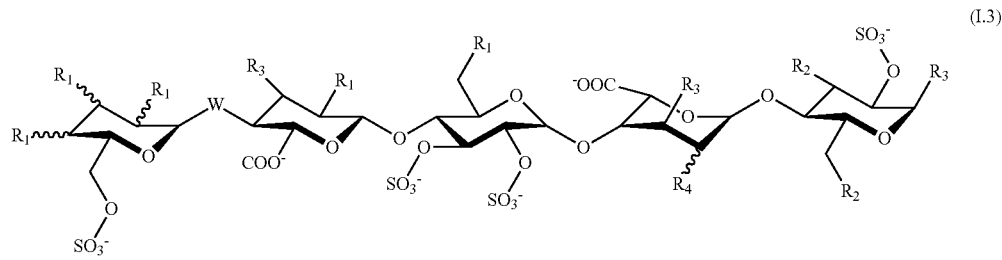
(I.3)

in which R$_1$, R$_2$, R$_3$, R$_4$ and W are as defined for (I), and also the pharmaceutically acceptable salts thereof.

Among these pentasaccharides of formula (I.3), the pentasaccharides in which just one of the substituents R$_1$, R$_2$, R$_3$ or R$_4$ represents an —NH—CO—(CH$_2$)$_5$—NH$_2$ group, and also the pharmaceutically acceptable salts thereof, constitute a subgroup of the invention.

Among these pentasaccharides of formula (I.3), a subject of the invention is also the pentasaccharides of formula (I.4):

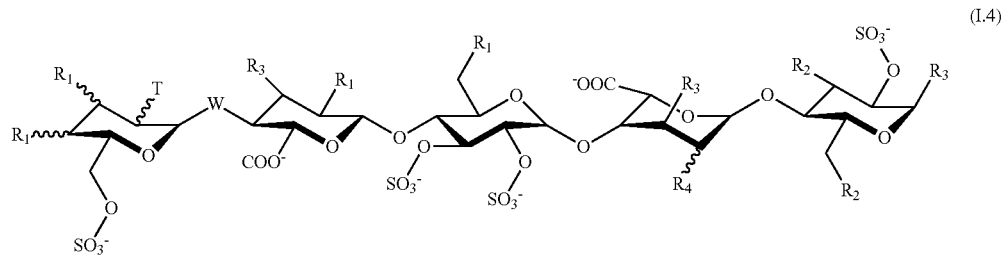
(I.4)

in which:
T represents an —NH—CO—(CH$_2$)$_5$—NH$_2$ group,
R$_1$ represents a (C$_1$-C$_6$)alkoxy group or an —OSO$_3^-$ group,
R$_2$ represents a (C$_1$-C$_6$)alkoxy group or an —OSO$_3^-$ group,
R$_3$ represents a (C$_1$-C$_6$)alkoxy group,
R$_4$ represents a (C$_1$-C$_6$)alkoxy group or an —OSO$_3^-$ group, or else R$_4$ constitutes an —OH—CH$_2$-bridge, the —CH$_2$— group being bonded to the carbon atom bearing the carboxylic function on the same ring,
W represents an oxygen atom or a methylene group,
and also the pharmaceutically acceptable salts thereof.

According to another of its aspects, the invention relates to the following polysaccharide:
methyl (2-[N-(6-aminohexanoyl)]-2-deoxy-3,4-di-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid (1→4)-2,3,6-tri-O-sulfonato-α-D-glucopyranoside sodium salt.

It is the pentasaccharide having the following formula (compound 1):

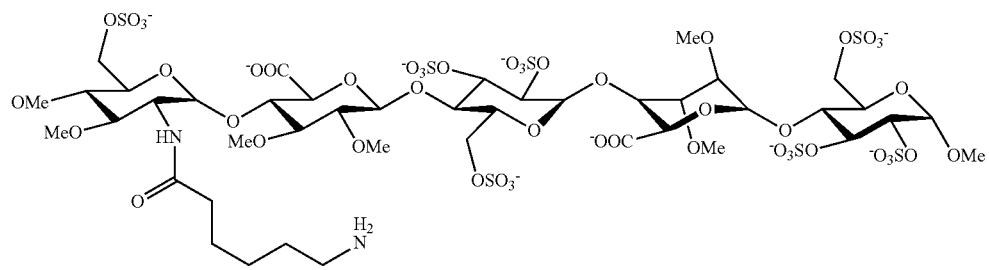

The invention encompasses the polysaccharides in the acid form thereof or in the form of any one of the pharmaceutically acceptable salts thereof. In the acid form, the —COO$^-$ and —SO$_3^-$ functions are, respectively, in —COOH and —SO$_3$H form.

The expression "pharmaceutically acceptable salt of the polysaccharides of the invention" is intended to mean a polysaccharide in which one or more of the —COO$^-$ and/or —SO$_3^-$ functions is (are) ionically bonded to a pharmaceutically acceptable cation. The preferred salts according to the invention are those of which the cation is chosen from alkali metal cations, and even more preferably those of which the cation is Na$^+$ or K$^+$.

The compounds of formula (I) above also comprise those in which one or more hydrogen or carbon atoms have been replaced with the radioactive isotope thereof, for example tritium or carbon-14. Such labeled compounds are of use in research, metabolism or pharmacokinetic studies, or in biochemical tests as ligands.

In its principle, the method for preparing the compounds according to the invention uses di- or oligosaccharide base synthons prepared as previously reported in the literature. Reference will in particular be made to patents or patent applications EP 0 300 099, EP 0 529 715, EP 0 621 282 and EP 0 649 854 and also to the document C. van Boeckel, M. Petitou, *Angew. Chem. Int. Ed. Engl.,* 1993, 32, 1671-1690. These synthons are then coupled to one another so as to provide an entirely protected equivalent of a polysaccharide according to the invention. This protected equivalent is then converted into a compound according to the invention.

One of the base synthons mentioned above contains a particular protected function allowing the subsequent introduction of the —CO—(CH$_2$)$_5$—NH$_2$ group (so as to form the —NH—CO—(CH$_2$)$_5$—NH$_2$ chain on the polysaccharide), for example a latent amine function in azido group form or protected in N-phthalimido form.

In the coupling reactions mentioned above, a "donor" di- or oligosaccharide, activated on its anomeric carbon, reacts with an "acceptor" di- or oligosaccharide having a free hydroxyl.

The present invention relates to a method for preparing the compounds of formula (I), characterized in that: in a first step, a completely protected equivalent of the desired polysaccharide (I), containing a protected precursor of the Pe domain extended at its nonreducing end by a protected precursor of the sulfated polysaccharide Po, is synthesized, one of these precursors containing in particular an amine function which is suitably protected for the subsequent introduction of the —CO—(CH$_2$)$_5$—NH$_2$ group, itself suitably protected; in a second step, the negatively charged groups are introduced and/or unmasked; in a third step, the amine function on the polysaccharide is deprotected and then the protected —CO—(CH$_2$)$_5$—NH$_2$ group is introduced; in a fourth step, the terminal NH$_2$ group is unmasked.

The synthesis of Pe is carried out according to the methods described in particular in the patent applications published under numbers WO 98/03554 and WO 99/36443, and also in the literature on polysaccharides.

The polysaccharide part which is the precursor of Po is synthesized according to reactions well known to those skilled in the art, using oligosaccharide synthesis methods (G. J. Boons, *Tetrahedron,* 1996, 52, 1095-1121, WO 98/03554 and WO 99/36443). Typically, a glycosidic-linkage donor oligosaccharide is coupled with a glycosidic-linkage acceptor oligosaccharide so as to produce another oligosaccharide, the size of which is equal to the sum of the sizes of the two reactive species. This sequence is repeated until the desired compound of formula (I) is obtained. The nature and the profile of the charge of the desired final compound determine the nature of the chemical entities used in the various steps of the synthesis, according to the rules well known to those skilled in the art. Reference may, for example, be made to C. van Boeckel, M. Petitou, *Angew. Chem. Int. Ed. Engl.,* 1993, 32, 1671-1690 or alternatively to H. Paulsen, "Advances in selective chemical syntheses of complex oligosaccharides" *Angew. Chem. Int. Ed. Engl.,* 21, 155-173 (1982).

The compounds of the invention are obtained from the completely protected polysaccharide precursors thereof using the following series of reactions:
the alcohol functions that must be converted into an O-sulfo group and the carboxylic acids are deprotected by removing the protective groups used during the production of the backbone,
the sulfo groups are then introduced, the amine function of the polysaccharide making it possible to introduce the —CO—$(CH_2)_5$—$NH_2$ group is deprotected, the suitably protected —CO—$(CH_2)_5$—$NH_2$ group is introduced by means of a conventional amino/acid coupling reaction, then the terminal-$NH_2$ group is unmasked.

The compounds of the invention can naturally be prepared using various strategies known to those skilled in the art of oligosaccharide synthesis.

The method described above is the preferred method of the invention. However, the compounds of formula (I) can be prepared by means of other methods that are well known in sugar chemistry, described, for example, in Monosaccharides, Their Chemistry and their roles in natural products, P. M. Collins and R. J. Ferrier, J. Wiley & Sons, 1995 and G. J. Boons, *Tetrahedron*, 1996, 52, 1095-1121.

The Pe pentasaccharides can therefore be obtained from disaccharide synthons in the manner described in the publication by C. van Boeckel, M. Petitou, *Angew. Chem. Int. Ed. Engl.*, 1993, 32, 1671-1690.

Generally, the protective groups used in the method for preparing the compounds (I) are those commonly used in sugar chemistry, as described, for example, in Protective Groups in Organic Synthesis, T W Greene, John Wiley & Sons, New York, 1981. The protective groups can, for example, be chosen from acetyl, halomethyl, benzoyl, levulinyl benzyl, substituted benzyl, optionally substituted trityl, tetrahydropyranyl, allyl, pentanyl, tert-butyldimethylsilyl (tBDMS) or trimethylsilylethyl groups.

The activating groups are those conventionally used in sugar chemistry according to, for example, G. J. Boons, *Tetrahedron*, 1996, 52, 1095-1121. These activating groups are chosen, for example, from imidates, thioglycosides, pentenylglycosides, xanthates, phosphites or halides.

In particular, the introduction of the —CO—$(CH_2)_5$—$NH_2$ group onto the free amine function of the polysaccharide, according to the method described above, can be carried out using a reactant of Act-CO—$(CH_2)_5$—NH-Pg type, in which "Act" represents an acid-function-activating group (such as an imide, for example a succinimide derivative, or else a mixed anhydride, or alternatively any other activating agent known in peptide chemistry for amino/acid coupling reactions) and "Pg" represents an amine-function-protecting group (such as a benzyloxycarbonyl group).

The method described above makes it possible to obtain the compounds of the invention in salt form. In order to obtain the corresponding acids, the compounds of the invention in salt form are brought into contact with an acid-form cation exchange resin. The compounds of the invention in acid form can then be neutralized with a base so as to obtain the desired salt. To prepare the salts of the compounds of formula (I), any inorganic or organic base which gives, with the compounds of formula (I), pharmaceutically acceptable salts can be used. Sodium hydroxide, potassium hydroxide, calcium hydroxide or magnesium hydroxide is preferably used as base. The sodium and calcium salts of the compounds of formula (I) are the preferred salts.

The invention will be understood more clearly by means of the detailed example which follows, relating to the preparation of a compound according to the invention of pentasaccharide type, corresponding to formula (I.4). This example is not limiting and merely illustrates the present invention.

EXAMPLE OF PREPARATION OF COMPOUND 1

Methyl(2-[N-(6-aminohexanoyl)]-2-deoxy-3,4-di-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt Compound 1

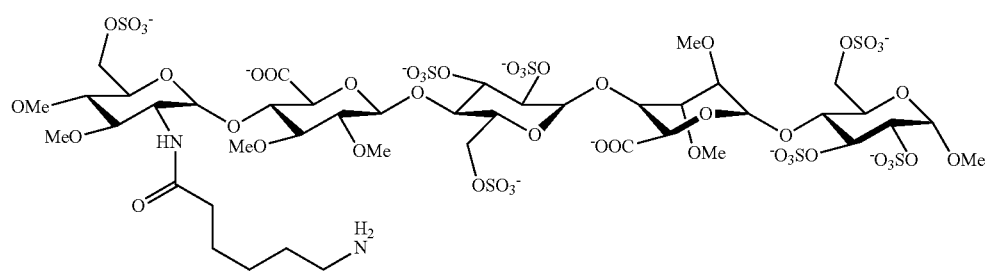

1) Preparation of succinimidyl 6-(benzyloxycarbonyl amino)hexanoate

Triethylamine (0.63 ml, 4.52 mmol) is added to a solution of 6-(benzyloxycarbonylamino)hexanoic acid (1.00 g, 3.77 mmol) in dimethylformamide (20 ml) and the mixture is left to stir at ambient temperature and under argon for 30 minutes. The solution is cooled to 0° C. and ethyl chloroformate (0.43 ml, 4.52 mmol) is added dropwise. After two hours at ambient temperature, N-hydroxysuccinimide (0.52 g, 4.52 mmol) is added and the mixture is left to stir overnight at ambient temperature. The mixture is evaporated to dryness before taking up the residue in water to which ethyl acetate is added. The phases are separated and the aqueous phase is extracted with ethyl acetate. The organic phases are combined, dried over sodium sulfate, filtered and evaporated to dryness before purification on a silica gel column with an ethyl acetate/pentane mixture (75/25 v/v) as eluent. The fractions, once evaporated, give 1.13 g of succinimidyl 6(benzyloxycarbonylamino)hexanoate in the form of an oil.

TLC: $R_f$=0.22 on silica gel plate with an n-heptane/ethyl acetate mixture (30/70 v/v) as eluent.

2) Preparation of compound 1'

The amino chain is grafted onto the pentasaccharide 44, or methyl (2-amino-2-deoxy-3,4-di-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt, the preparation of which is described in patent application WO 02/24754:

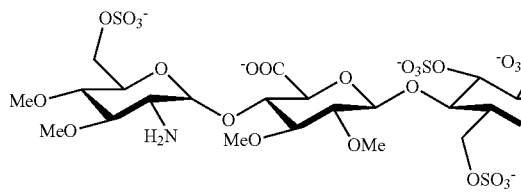

44

The pentasaccharide 44 (505 mg, 0.29 mmol) is added to a solution of succinimidyl 6-(benzyloxycarbonyl-amino)hexanoate (783 mg, 2.16 mmol) in N,N-dimethyl-formamide (10 ml). After stirring for 24 hours in an inert atmosphere and at ambient temperature, the solvent is evaporated off under reduced pressure and the residue is dissolved in water (40 ml), before washing the solution with chloroform (2×30 ml). The chloroform phase is washed with water (10 ml) and the aqueous phases are combined, and then evaporated to dryness under reduced pressure. The solid residue is triturated with 2-propanol (10 ml) and the suspension is centrifuged for 5 minutes at 2500 rpm. The alcoholic phase is drawn off and replaced with 2-propanol (10 ml), and the centrifugation is repeated. After having drawn off the solvent, the crude product is dried under vacuum.

399 mg of compound 1', or methyl (2-[N-(6-benzyloxycarbonylaminohexanoyl)]-2-deoxy-3,4-di-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, in which Pg represents a benzyloxycarbonyl group, are thus obtained:

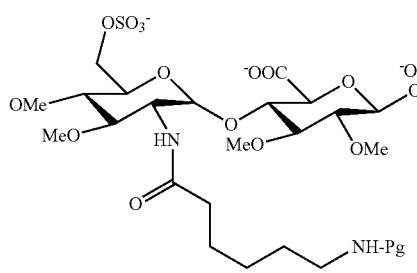

Compound 1'

Proton NMR at 200 MHz in deuterated water: the structure of the expected product is confirmed, owing to the fact that the spectrum obtained is identical to that produced on a product synthesized in accordance with example 5 of patent application WO 02/24754, without the signals due to the atoms of the biotin part, but with signals of 7.4 to 7.5 ppm due to the benzyloxy group.

3) Preparation of compound 1

The product 1' obtained at the end of the preceding step (399 mg) is dissolved in deuterated water (10 ml). The solution is treated with palladium-on-carbon at 10% (25 mg) and the solution is left to stir for 20 hours in the presence of hydrogen at atmospheric pressure. The mixture is diluted with water (15 ml), the catalyst is filtered off, and the solution is washed with chloroform (2×15 ml) before carrying out evaporation to dryness under reduced pressure. An aliquot (98

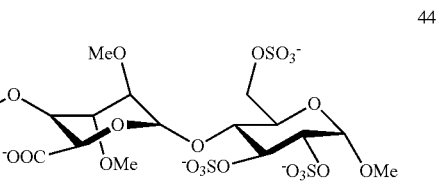

mg out of 320 mg) of this product is purified on a Sephadex G-25 gel column (2.5×50 cm) with water as eluent, to give 25 mg of compound 1.

HPLC: Tr=15.4 min on X-Terra RP-18 150×4.6 mm column, particles of 5µ, from Waters SA. Detection with UV lamp at 211 nm. Eluent 1: water containing 0.02 M of ammonium acetate and 0.05 M of di-N-butylamine, adjusted to pH 7 with acetic acid. Eluent 2: acetonitrile/water mixture (90/10 v/v) containing 0.05 M of di-N-butylamine and 0.08 M of acetic acid. The proportions of the eluents are programmed such that the eluent-2 composition is 10% at 0 min; 20% at 25 min; 50% at 40 min; 50% at 43 min, and 5% at 50 minutes.

Proton NMR at 600 MHz in deuterated water: the structure of the expected product is confirmed, owing to the fact that the spectrum obtained is identical to that produced on a product synthesized in accordance with example 5 of patent application WO 02/24754, without the signals due to the atoms of the biotin part.

Pharmacology:

The compounds according to the invention were the subject of biochemical and pharmacological studies.

The pharmacological activity of these products was in particular studied in an in vitro model of inhibition of coagulation factor Xa, in the presence of antithrombin (anti-factor Xa activity dependent on the presence of antithrombin), as described by J.-M. Herbert et al., *Blood,* 1998, 91, 4197-4205. In this model, the antithrombotic properties of the compounds according to the invention are confirmed. In particular, for compound 1 according to the invention, IC50=1.69×10$^{-2}$ µg/ml (IC50: dose for 50% inhibition).

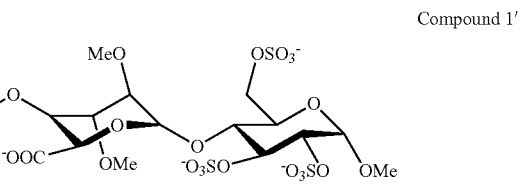

By virtue of their biochemical and pharmaceutical activity, the oligosaccharides of the present invention constitute very advantageous medicaments. Their toxicity is perfectly compatible with this use. They are also very stable and are therefore particularly suitable for constituting the active ingredient of patent medicines.

They can be used in various pathological conditions subsequent to a modification of the homeostasis of the coagulation system occurring in particular during cardiovascular and cerebrovascular system disorders, for instance thromboembolic disorders associated with atherosclerosis and with diabetes, such as unstable angina, stroke, post-angioplasty restenosis, endarterectomy, the insertion of endovascular prostheses; or thromboembolic disorders associated with post-thrombolysis rethrombosis, with infarction, with dementia of ischemic origin, with peripheral arterial disorders, with hemodialysis, with arterial fibrillation or else during the use of vascular prostheses for aortocoronary bypasses. These products can, moreover, be used for the treatment or prevention of thromboembolic pathological conditions of venous origin, such as pulmonary embolisms and deep vein thrombosis. They can be used either for preventing or for treating the thrombotic complications observed, for example, following surgical operations, the growth of tumors or coagulation disturbances induced by bacterial, viral or enzymatic activators. In the case of their use during the insertion of prostheses, the compounds of the present invention can cover prostheses and thus make them hemocompatible. In particular, they can be attached to intravascular prostheses (stents). In this case, they can optionally be chemically modified by introduction, at the nonreducing or reducing end, of an appropriate arm, as described according to EP 649 854. The compounds of the present invention can also be used as adjuvants during endarterectomy carried out with porous balloons.

The compounds according to the invention can be used for the preparation of medicaments intended for treating or preventing the above diseases.

According to another of the aspects of the present invention, a subject thereof is therefore a pharmaceutical composition containing, as active ingredient, a synthetic polysaccharide according to the invention or a pharmaceutically acceptable salt thereof, optionally in combination with one or more suitable inert excipients. Said excipients are chosen according to the pharmaceutical form and the mode of administration desired: oral, sublingual, subcutaneous, intramuscular, intravenous, transdermal, transmucosal, local or rectal.

The active ingredient can also be provided in the form of a complex with a cyclodextrin, for example α-, β- or γ-cyclodextrin, 2-hydroxypropyl-β-cyclodextrin or methyl-β-cyclodextrin.

The active ingredient can also be released by a balloon containing it or by an endovascular expander inserted into the blood vessels. The pharmacological efficacy of the active ingredient is thus not affected.

In each dosage unit, the active ingredient is present in the amounts suitable for obtaining the desired prophylactic or therapeutic effect. Each dosage unit can contain from 0.1 to 100 mg of active ingredient, preferably 0.5 to 50 mg, more preferably from 2.5 to 3.0 mg.

The compounds according to the invention can also be used in combination with one or more other active ingredients that are of use for the desired therapy, such as, for example, antithrombotics, anticoagulants, platelet aggregation inhibitors agents, for instance dipyridamole, aspirin, ticlopidine, clopidogrel, or glycoprotein IIb/IIIa complex antagonists.

The invention claimed is:

1. A synthetic polysaccharide with antithrombotic activity, corresponding to the formula:

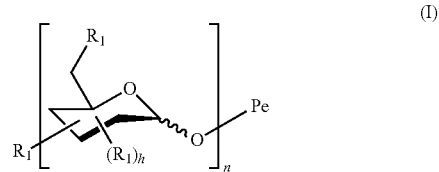

(I)

wherein:
the wavy line denotes a bond located either below or above the plane of the pyranose ring, and
the formula:

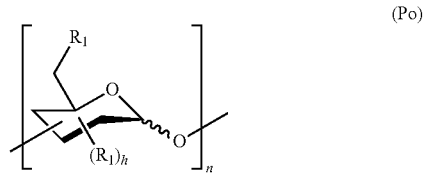

(Po)

denotes a polysaccharide containing n identical or different monosaccharide units, said polysaccharide being bonded via its anomeric carbon to Pe, and
the formula:

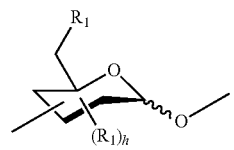

is a diagrammatic representation of a monosaccharide unit with a pyranose structure, chosen from hexoses, pentoses and the corresponding deoxy sugars, this unit being bonded via its anomeric carbon to another monosaccharide unit, and the hydroxyl groups of this unit being substituted with groups $R_1$, which may be identical or different, $R_1$ being as defined below, and Pe represents a pentasaccharide having the structure:

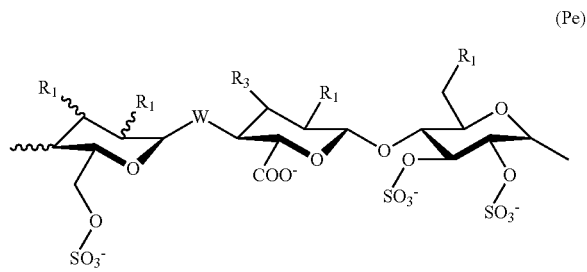

(Pe)

-continued

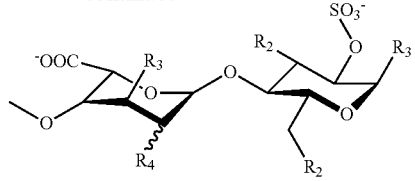

wherein
h is equal to 1 or 2, and
n is an integer and can take any value from 0 to 25, and
$R_1$ represents an —NH—CO—$(CH_2)_5$—$NH_2$ group, a $(C_1$-$C_6)$alkoxy group or an —$OSO_3^-$ group; and
$R_2$ represents an —NH—CO—$(CH_2)_5$—$NH_2$ group, a $(C_1$-$C_6)$alkoxy group or an —$OSO_3^-$ group; and
$R_3$ represents an —NH—CO—$(CH_2)_5$—$NH_2$ group or a $(C_1$-$C_6)$alkoxy group; and
$R_4$ represents an —NH—CO$(CH_2)_5$—$NH_2$ group, a $(C_1$-$C_6)$alkoxy group or an —$OSO_3^-$ group or else $R_4$ constitutes an —O—$CH_2$ bridge, the —$CH_2$— group being bonded to the carbon atom bearing the carboxylic function on the same ring; and
wherein at least one of the substituents $R_1$, $R_2$, $R_3$ or $R_4$ represents an —NH—CO—$(CH_2)_5$—$NH_2$ group; and wherein
W represents an oxygen atom or a methylene group, and pharmaceutically acceptable salts thereof.

2. The polysaccharide according to claim 1, corresponding to formula (I.1):

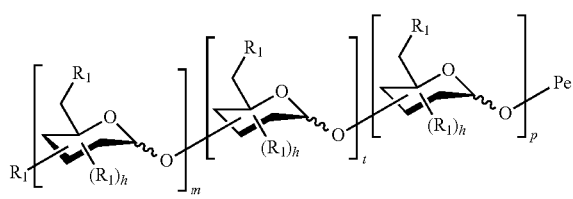

wherein:
the formula:

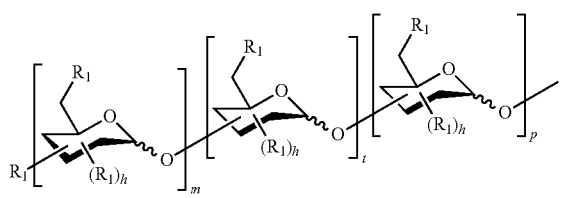

denotes a polysaccharide Po, bonded via its anomeric carbon to Pe as defined in claim 1, and
the formula:

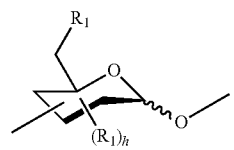

is as defined in claim 1, wherein
the $R_1$ groups are as defined in claim 1 and, for the same monosaccharide, may be identical or different, and
the monosaccharide contained in [ ]$_m$ is repeated m times, the monosaccharide contained in [ ]$_t$ is repeated t times, the monosaccharide contained in [ ]$_p$ is repeated p times, and wherein
m is an integer ranging from 1 to 5, t is an integer ranging from 0 to 24 and p is an integer ranging from 0 to 24, wherein $1 \leq m+t+p \leq 25$, and pharmaceutically acceptable salts thereof.

3. The polysaccharide according to claim 2, wherein just one of the substituents $R_1$, $R_2$, $R_3$ or $R_4$ represents an —NH—CO—$(CH_2)_5$—$NH_2$ group, and pharmaceutically acceptable salts thereof.

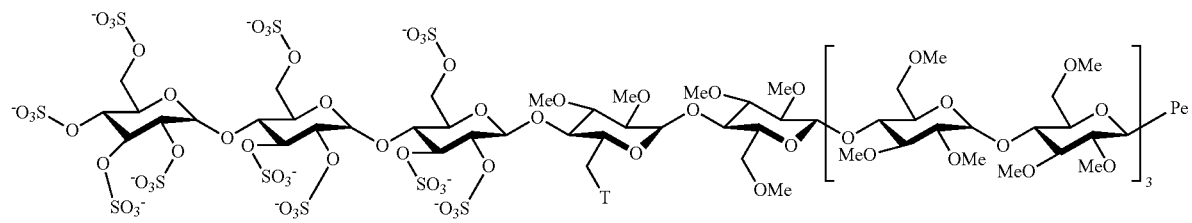

4. The polysaccharide according to claim 1 wherein said polysaccharide is of formula (I.2):
   wherein:
   T represents an —NH—CO—(CH$_2$)$_5$—NH$_2$ group, and
   Pe represents a pentasaccharide having the structure:

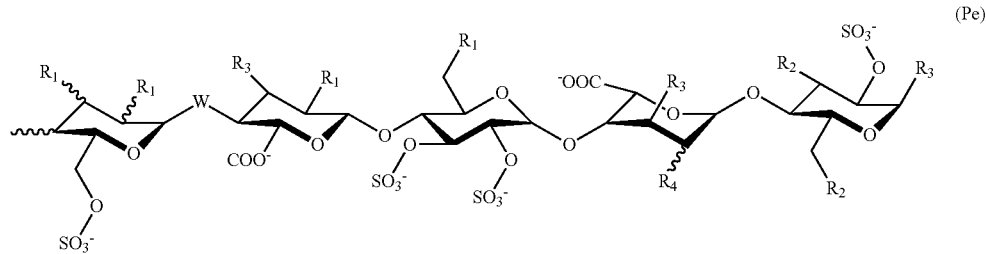

(Pe)

wherein in which:
   R$_1$ represents a (C$_1$-C$_6$)alkoxy group or an —OSO$_3^-$ group, and
   R$_2$ represents a (C$_1$-C$_6$)alkoxy group or an —OSO$_3^-$ group, and
   R$_3$ represents a (C$_1$-C$_6$)alkoxy group, and
   R$_4$ represents a (C$_1$-C$_6$)alkoxy group or an —OSO$_3^-$ group, or else R$_4$ constitutes an —O—CH$_2$ bridge, the —CH$_2$— group being bonded to the carbon atom bearing the carboxylic function on the same ring, and wherein
   W represents an oxygen atom or a methylene group, and pharmaceutically acceptable salts thereof.

5. The polysaccharide according to claim 1, wherein said polysaccharide is a pentasaccharide of formula (I.3):

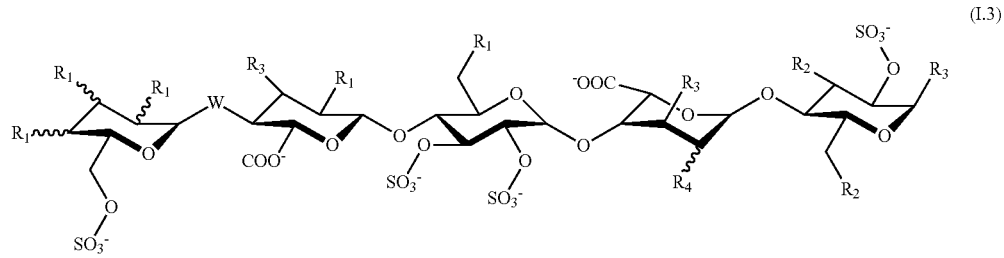

(I.3)

wherein R$_1$, R$_2$, R$_3$, R$_4$ and W are as defined in claim 1, and pharmaceutically acceptable salts thereof.

6. The polysaccharide according to claim 5, wherein said pentasaccharide comprises just one of the substituents R$_1$, R$_2$, R$_3$ or R$_4$ represents an —NH—CO—(CH$_2$)$_5$—NH$_2$ group, and pharmaceutically acceptable salts thereof.

7. The polysaccharide according to claim 5 wherein said pentasaccharide corresponds to formula (I.4):

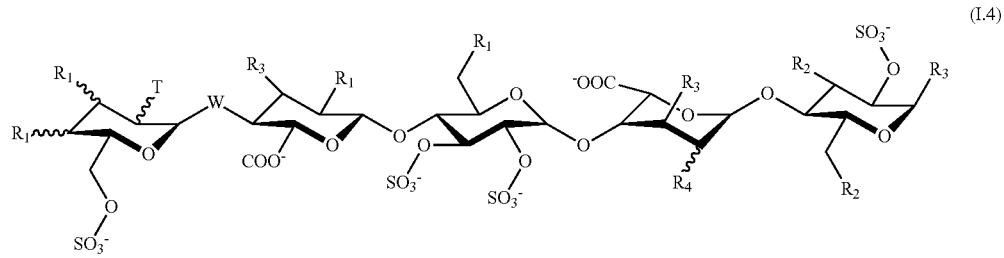

(I.4)

wherein:

T represents an —NH—CO—$(CH_2)_5$—$NH_2$ group, and $R_1$ represents a $(C_1$-$C_6)$alkoxy group or an —$OSO_3^-$ group, and $R_2$ represents a $(C_1$-$C_6)$alkoxy group or an —$OSO_3^-$ group, and $R_3$ represents a $(C_1$-$C_6)$alkoxy group, and $R_4$ represents a $(C_1$-$C_6)$alkoxy group or an —$OSO_3^-$ group, or else $R_4$ constitutes an —O—$CH_2$ bridge, the —$CH_2$— group being bonded to the carbon atom bearing the carboxylic function on the same ring, and wherein W represents an oxygen atom or a methylene group, and pharmaceutically acceptable salts thereof.

8. The polysaccharide according to claim 1, wherein the polysaccharide is methyl (2-[N-(6-aminohexanoyl)]-2-deoxy-3,4-di-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside sodium salt.

9. A pharmaceutical composition comprising, as an active ingredient, the polysaccharide according to claim 1, and one or more suitable inert excipients.

10. A method of treating a thromboembolic disorder in a patient in need thereof comprising administering to said patient a therapeutically effective amount of the pharmaceutical composition of claim 9.

* * * * *